United States Patent
Shin et al.

(10) Patent No.: US 11,875,659 B2
(45) Date of Patent: Jan. 16, 2024

(54) PRIVACY-PRESERVING RADAR-BASED FALL MONITORING

(71) Applicant: Google LLC, Mountain View, CA (US)

(72) Inventors: Dongeek Shin, San Jose, CA (US); Shwetak Patel, Seattle, WA (US); Rizwan Chaudhry, Millbrae, CA (US); Chetan Bhole, Mountain View, CA (US); Vaibhav Darbari, New York, NY (US); Todd Whitehurst, Belmont, CA (US); Anupam Pathak, San Carlos, CA (US)

(73) Assignee: Google LLC, Mountain View, CA (US)

( * ) Notice: Subject to any disclaimer, the term of this patent is extended or adjusted under 35 U.S.C. 154(b) by 0 days.

(21) Appl. No.: 17/784,024

(22) PCT Filed: Dec. 12, 2019

(86) PCT No.: PCT/US2019/065958
§ 371 (c)(1),
(2) Date: Jun. 9, 2022

(87) PCT Pub. No.: WO2021/118570
PCT Pub. Date: Jun. 17, 2021

(65) Prior Publication Data
US 2023/0018686 A1    Jan. 19, 2023

(51) Int. Cl.
*G08B 21/04* (2006.01)
*G01S 13/32* (2006.01)
*G01S 13/58* (2006.01)

(52) U.S. Cl.
CPC ............ *G08B 21/043* (2013.01); *G01S 13/32* (2013.01); *G01S 13/58* (2013.01); *G08B 21/0469* (2013.01)

(58) Field of Classification Search
CPC ... G08B 21/043; G08B 21/0469; G01S 13/32; G01S 13/58; G01S 7/414; G01S 7/415;
(Continued)

(56) References Cited

U.S. PATENT DOCUMENTS 8,063,764 B1 * 11/2011 Mihailidis .......... G08B 21/0492
340/539.18
8,520,784 B1    8/2013 Lackey
(Continued)

FOREIGN PATENT DOCUMENTS

AU    2012-308234 A1    5/2014
EP    3 511 732 A2    7/2019
(Continued)

OTHER PUBLICATIONS

International Search Report and Written Opinion for PCT/US2019/065958 dated Aug. 21, 2020, all pages.
(Continued)

*Primary Examiner* — Curtis J King
(74) *Attorney, Agent, or Firm* — Kilpatrick Townsend & Stockton LLP

(57) ABSTRACT

Various arrangements for performing fall detection are presented. A smart-home device (110, 201), comprising a monolithic radar integrated circuit (205), may transmit radar waves. Based on reflected radar waves, raw waveform data may be created. The raw waveform data may be processed to determine that a fall by a person (101) has occurred. Speech may then be output announcing that the fall has been detected via the speaker (217) of the smart home device (110, 201).

19 Claims, 7 Drawing Sheets

(58) Field of Classification Search
CPC ........ G01S 13/34; G01S 13/536; G01S 13/72;
G01S 13/86; G01S 13/88; G01S 7/35;
A61B 5/741; A61B 5/0507; A61B 5/1117;
A61B 5/6889; A61B 5/7267; A61B 5/747
See application file for complete search history.

(56) References Cited

U.S. PATENT DOCUMENTS

| | | | |
|---|---|---|---|
| 8,740,793 B2* | 6/2014 | Cuddihy | A61B 5/4806 600/301 |
| 8,742,935 B2* | 6/2014 | Cuddihy | G08B 21/0469 340/573.7 |
| 9,754,471 B2 | 9/2017 | Berezhnyy et al. | |
| 10,058,290 B1 | 8/2018 | Proud | |
| 10,206,610 B2* | 2/2019 | Al-Alusi | A61B 5/1112 |
| 10,417,923 B2 | 9/2019 | Walter et al. | |
| 10,690,763 B2 | 6/2020 | Shouldice et al. | |
| 10,901,069 B2* | 1/2021 | Otsuki | G08B 21/0423 |
| 11,074,800 B2* | 7/2021 | Li | G01S 13/89 |
| 11,250,683 B2* | 2/2022 | Sundholm | G08B 21/0461 |
| 11,250,942 B1 | 2/2022 | Ahmad et al. | |
| 11,257,346 B1* | 2/2022 | Meyers | G08B 27/005 |
| 11,426,120 B2* | 8/2022 | Cho | A61B 5/1118 |
| 2003/0011516 A1 | 1/2003 | Moch | |
| 2003/0058111 A1* | 3/2003 | Lee | G08B 13/19641 348/E7.086 |
| 2008/0081657 A1 | 4/2008 | Suzuki et al. | |
| 2008/0300572 A1 | 12/2008 | Rankers et al. | |
| 2010/0153045 A1 | 6/2010 | Teshirogi et al. | |
| 2010/0283845 A1 | 11/2010 | Yokochi et al. | |
| 2011/0060215 A1 | 3/2011 | Tupin, Jr. et al. | |
| 2011/0190594 A1 | 8/2011 | Heit et al. | |
| 2013/0002434 A1* | 1/2013 | Cuddihy | G01S 13/18 342/28 |
| 2013/0053653 A1* | 2/2013 | Cuddihy | A61B 5/0816 600/301 |
| 2013/0100268 A1* | 4/2013 | Mihailidis | G08B 21/02 348/77 |
| 2013/0143519 A1* | 6/2013 | Doezema | A61B 5/681 455/404.2 |
| 2013/0244644 A1 | 9/2013 | Amirijoo et al. | |
| 2014/0062702 A1* | 3/2014 | Rubio Andres | G08B 29/188 340/573.1 |
| 2014/0340227 A1* | 11/2014 | Reed, Jr. | A61B 5/6889 340/573.1 |
| 2016/0015315 A1 | 1/2016 | Auphan et al. | |
| 2016/0328941 A1* | 11/2016 | Sundholm | G08B 13/1618 |
| 2017/0221335 A1* | 8/2017 | Brillaud | A61B 5/1115 |
| 2018/0008169 A1* | 1/2018 | Chang | A61B 5/747 |
| 2018/0078735 A1 | 3/2018 | Dalgleish et al. | |
| 2018/0322351 A1 | 11/2018 | Shaker | |
| 2018/0329049 A1 | 11/2018 | Amihood et al. | |
| 2018/0330589 A1 | 11/2018 | Horling | |
| 2018/0330593 A1 | 11/2018 | Zack et al. | |
| 2018/0367952 A1* | 12/2018 | Devdas | G08B 21/043 |
| 2019/0108742 A1* | 4/2019 | Stolbikov | G08B 19/00 |
| 2019/0108913 A1* | 4/2019 | Coke | A61B 5/0507 |
| 2019/0117125 A1* | 4/2019 | Zhang | A61B 5/0077 |
| 2019/0130725 A1* | 5/2019 | Dempsey | G08B 19/00 |
| 2019/0187268 A1 | 6/2019 | Lien et al. | |
| 2019/0391249 A1 | 12/2019 | Takeuchi et al. | |
| 2020/0033470 A1 | 1/2020 | Brankovic et al. | |
| 2020/0118410 A1* | 4/2020 | Lindström | G08B 7/06 |
| 2020/0146550 A1* | 5/2020 | Tunnell | H04L 65/4015 |
| 2020/0166611 A1* | 5/2020 | Lin | G01S 13/0209 |
| 2020/0178892 A1 | 6/2020 | Maslik et al. | |
| 2020/0195327 A1 | 6/2020 | Thiagarajan et al. | |
| 2020/0253508 A1 | 8/2020 | Campbell | |
| 2020/0289033 A1* | 9/2020 | Sivertsen | A61B 5/1115 |
| 2020/0367810 A1 | 11/2020 | Shouldice et al. | |
| 2020/0408876 A1 | 12/2020 | Weber et al. | |
| 2020/0410072 A1 | 12/2020 | Giusti et al. | |
| 2021/0030276 A1 | 2/2021 | Li et al. | |
| 2021/0037315 A1 | 2/2021 | Eckert et al. | |
| 2021/0088643 A1 | 3/2021 | Hayashi et al. | |
| 2021/0142643 A1* | 5/2021 | Susna | A61B 5/7264 |
| 2021/0150873 A1 | 5/2021 | Shouldice et al. | |
| 2021/0217288 A1* | 7/2021 | Sundholm | G08B 21/0461 |
| 2021/0244352 A1 | 8/2021 | Campbell et al. | |
| 2021/0256829 A1* | 8/2021 | Ten Kate | G08B 21/0446 |
| 2021/0264762 A1* | 8/2021 | Lunner | G08B 21/22 |
| 2021/0298643 A1* | 9/2021 | Baker | A61B 5/0004 |
| 2022/0268916 A1* | 8/2022 | Nagpal | H04R 1/406 |
| 2023/0037749 A1* | 2/2023 | Kadam | G16H 50/20 |

FOREIGN PATENT DOCUMENTS

| | | |
|---|---|---|
| WO | 2009/105418 A1 | 8/2009 |
| WO | 2018-050913 A1 | 3/2018 |
| WO | 2018/220087 A1 | 12/2018 |
| WO | 2019-122413 A1 | 6/2019 |
| WO | 2019-202385 A1 | 10/2019 |
| WO | 2020-104465 A2 | 5/2020 |
| WO | 2020-176100 A1 | 9/2020 |
| WO | 2020-176105 A1 | 9/2020 |
| WO | 2020/226638 A1 | 11/2020 |
| WO | 2021-107958 A1 | 3/2021 |
| WO | 2021/137120 A1 | 7/2021 |
| WO | 2022006183 A1 | 1/2022 |

OTHER PUBLICATIONS

International Search Report and Written Opinion for PCT/US2019/066305 dated Sep. 10, 2020, all pages.

International Search Report and Written Opinion dated Apr. 30, for PCT/US2020/048388, 20 pages.

Yang. F., et al., "EM techniques for the detection of breast cancer," 2010 IEEE Antennas and Propagation Society International Symposium, (Year 2010), pp. 1-4, doi: 10.1109/APS.2010.5562289.

"S+ by ResMed" [Web page], (n.d.). Retrieved on Jul. 10, 2020 from https://splus.resmed.com/, 9 pages.

"X4" (n.d.). Retrieved on Jul. 10, 2020 from Novelda website https://novelda.com/x4-soc.html, 3 pages.

"Novelda Presence Sensor" (n.d.). Retrieved on Aug. 13, 2020 from Novelda website https://novelda.com/novelda-presence-sensor.html, 1 page.

"A World Leader Within Ultra Wideband (UWB) Sensing", (n.d.). Retrieved on Aug. 14, 2020 from Novelda website https://novelda.com/, 2 pages.

Tran, V.P., et al., "Doppler Radar-Based Non-Contact Health Monitoring for Obstructive Sleep Apnea Diagnosis: A Comprehensive Review", Big Data and Cognitive Computing, vol. 3, Issue 1, Jan. 1, 2019, DOI: 10.3390/bdcc3010003, 21 pages.

International Search Report and Written Opinion for PCTUS2020051776 dated Jun. 18, 2021, all pages.

International Search Report and Written Opinion for PCTUS2021040643 dated Dec. 13, 2021, all pages.

* cited by examiner

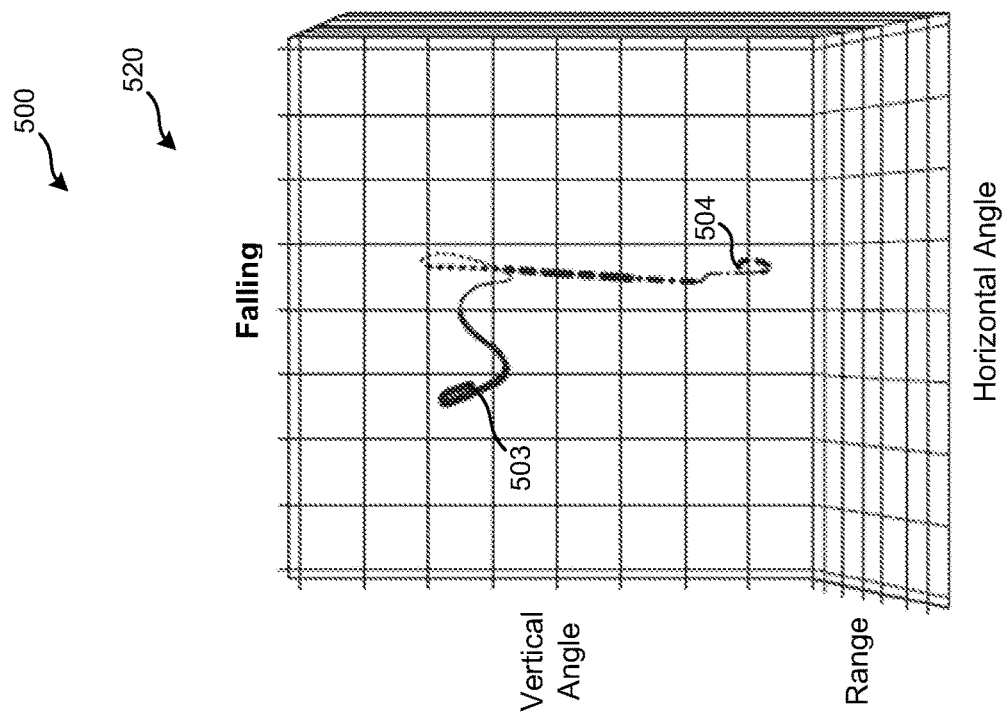
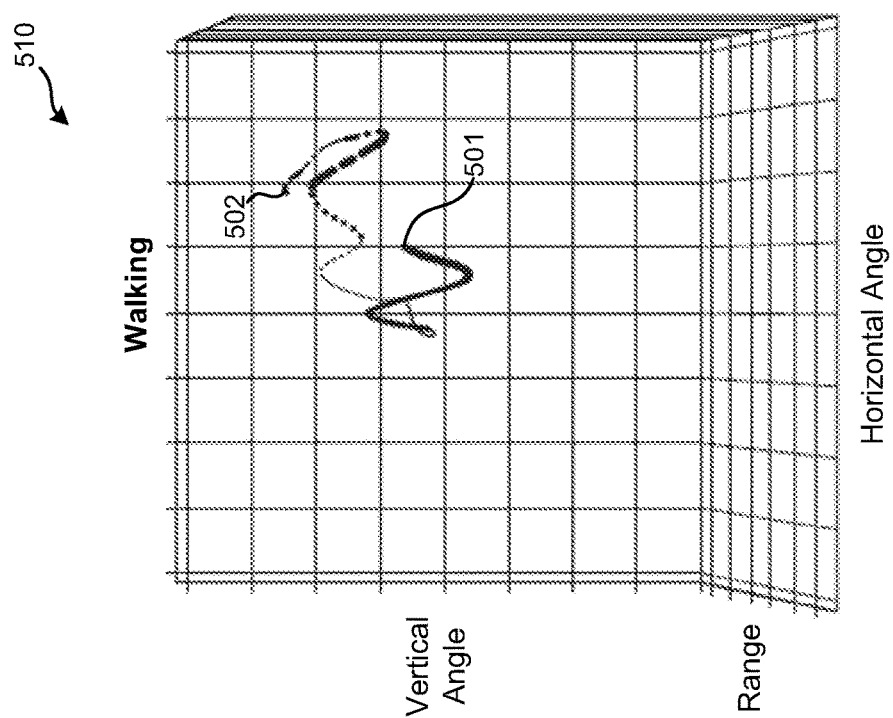
FIG. 5

PRIVACY-PRESERVING RADAR-BASED FALL MONITORING

CROSS-REFERENCE TO RELATED APPLICATIONS

This application is a 371 National Stage filing of PCT Application No. PCT/US2019/065958, filed Dec. 12, 2019, and titled "PRIVACY-PRESERVING RADAR-BASED FALL MONITORING," which is hereby incorporated by reference in its entirety for all purposes.

BACKGROUND

A wearable device that determines if a person has fallen is only useful if the person remembers to use it properly, such as keeping the wearable device charged and worn properly. For at least some of the population that is most at-risk for falling, such proper use may be difficult to sustain. Therefore, it may be desirable to monitor a person at-risk for falling without requiring the person to wear any wearable device.

While cameras can be used to capture images of an environment, such images can lead to privacy concerns. From these images, it can be possible to identify persons based on their facial features or other physical characteristics. Therefore, some people may not feel comfortable having a camera installed at their home, especially in some private locations, such as bedrooms and bathrooms.

SUMMARY

Various embodiments are described related to a smart-home device with integrated fall detection. In some embodiments, a smart-home device with integrated fall detection is described. The device may include a housing. The device may include a speaker within the housing. The device may include a microphone within the housing. The device may include a monolithic radar integrated circuit that may comprise an antenna array for receiving reflected radar. The monolithic radar integrated circuit may emit radar at greater than 40 GHz. The monolithic radar integrated circuit may be housed by the housing. The device may include a processing system, comprising one or more processors, that may be in communication with the monolithic radar integrated circuit. The system may be configured to receive raw waveform data from the radar integrated circuit. The system may be configured to process the raw waveform data to determine that a fall by a person has occurred. The system may be configured to output an indication that the fall has been detected.

Embodiments of such a method may include one or more of the following features: the monolithic radar integrated circuit may have dimensions of less than 8 mm by 6 mm by 2 mm. The processing system being configured to output the indication may comprise the processing system being configured to cause the speaker of the smart-home device to output speech announcing that the fall has been detected and request that an auditory response be provided. The processing system may be further configured to receive an auditory response via the microphone and process the auditory response. The processing system may be further configured to perform an action in response to the auditory response. The action may be transmitting a communication via a wireless network to an emergency contact. The action may be outputting a spoken message indicating that no further action may be taken. The monolithic radar integrated circuit may emit frequency-modulated continuation wave (FMCW) radio waves. The smart-home device may be a home assistant device. The processing system may be further configured to filter, from the raw waveform data, waveform data indicative of static objects to obtain motion-indicative waveform data. The processing system may be further configured to perform center-of-mass tracking on a moving object present within the motion-indicative waveform data. The processing system may be further configured to classify the moving object based on the center-of-mass tracking using a pre-trained machine learning model. The processing system being configured to output an indication that the fall has been detected may be based on the processing system classifying the moving object based on the center-of-mass tracking using the pre-trained machine learning model. The processing system being configured to classify the moving object based on the center-of-mass tracking using the pre-trained machine learning model may comprise applying a random forest pre-trained machine learning model. The pre-trained machine learning model as installed on the smart-home device may be static and was created based on a training set of data indicative of situations in which a person has fallen and in which a person has not fallen. The processing system being configured to perform center-of-mass tracking may comprise the processing system being configured to perform center-of-mass tracking over a rolling historic time period window. The rolling historic time period window may be between one and fifteen seconds. The processing system may be further configured to create a plurality of heat maps based on the motion-indicative waveform data. Each heat map of the plurality of heat maps may be indicative of detected motion at a plurality of distances in a plurality of directions along a particular axis. The processing system being configured to receive the raw waveform data may comprise the processing system being configured to receive a plurality of individual sets of raw waveform data from a plurality of antennas of the antenna array of the monolithic radar integrated circuit. The processing system being configured to classify the moving object may be performed by the processing system based on at least four physical features of the center-of-mass tracking.

In some embodiments, a method for performing fall detection is described. The method may comprise positioning a home assistant device with a room such that the home assistant device may be intended to remain stationary. The home assistant device may comprise a speaker. The home assistant device may comprise a microphone. The home assistant device may comprise a monolithic radar integrated circuit that may comprise an antenna array for receiving reflected radar. The method may comprise transmitting, by the home assistant device, radar waves within the room. The method may comprise, based on reflected radar waves within the room, creating raw waveform data. The method may comprise processing, by the home assistant device, the raw waveform data to determine that a fall by a person has occurred. The method may comprise outputting, by the home assistant device, speech announcing that the fall has been detected via the speaker of the home assistant device.

Embodiments of such a method may include one or more of the following features: An auditory response may be received via the microphone of the home assistant device. The method may further comprise performing an action in response to the auditory response. The action may be transmitting a communication via a wireless network to an emergency contact. The action may be outputting a spoken message indicating that no further action may be taken. Processing the raw waveform data to determine that the fall by the person has occurred may comprise filtering, from the raw waveform data, waveform data indicative of static objects to obtain motion-indicative waveform data. Processing the raw waveform data to determine that the fall by the person has occurred may comprise performing center-of-mass tracking on a moving object present within the motion-indicative waveform data. Processing the raw waveform data to determine that the fall by the person has occurred may comprise classifying the moving object based on the center-of-mass tracking using a pre-trained machine learning model. Outputting the speech announcing that the fall has been detected may be based on the pre-trained machine learning model classifying the moving object based on the center-of-mass tracking. Classifying the moving object based on the center-of-mass tracking using the pre-trained machine learning model may comprise applying a random forest pre-trained machine learning model.

BRIEF DESCRIPTION OF THE DRAWINGS

A further understanding of the nature and advantages of various embodiments may be realized by reference to the following figures. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 5 illustrates embodiments of two tracklets.

DETAILED DESCRIPTION

Figure 1:
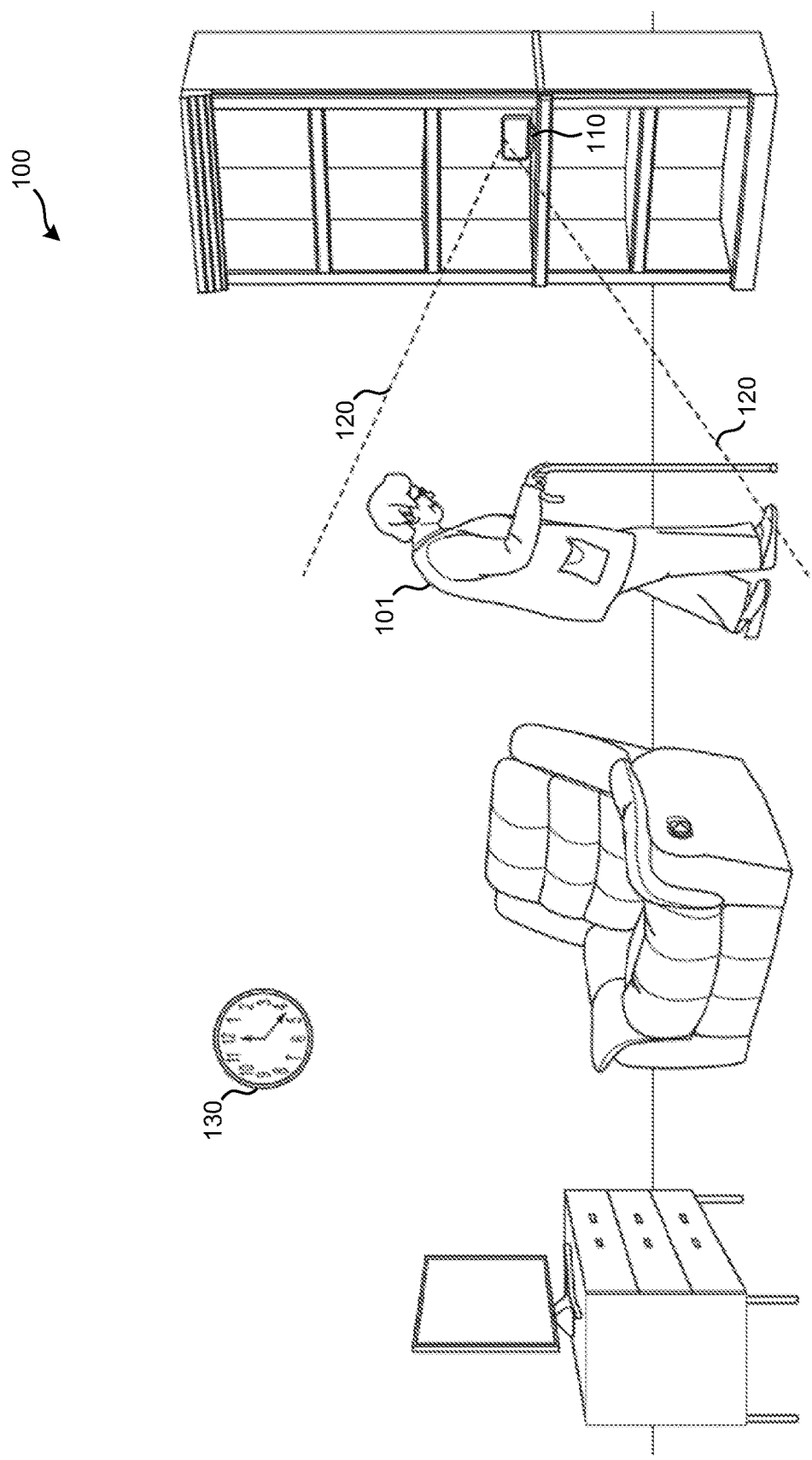
FIG. 1 illustrates an embodiment of an environment in which a person can be monitored for falls.

Radar can function as a superior technology for monitoring an environment for a person falling compared to camera-based technologies. Radar can be used to accurately determine a location and range of person, while not gathering sufficient information to violate the person's privacy. For instance, from information gathered using radar, it may be possible to determine where a person is located and whether the person is standing, but "image-quality" features may not be captured. Optical imaging performed using cameras or video equipment tend to cross a line when it comes to traditional notions of privacy. In contrast, radar sensing does not yield information sufficient to support optical images that would be of a privacy concern. Even if usable to identify height, type of species (e.g., human or animal), and specialized motions such as gestures, any radar "images" that might be formed from computations, even those from which some aspect of an identity or characteristic might be derivable, tend not to be of concern with regard to traditional notions of privacy, because such radar "images" would tend to be more blob-like, ghost-like, or phantom-like. Therefore, it may be acceptable to use radar technology in areas where the person expects privacy, such as in a bedroom or bathroom.

As detailed herein, by using high-frequency radar, such as above 50 GHz, a monolithic radar integrated circuit (or a "radar chip") can be used that includes all radar componentry on-board. For instance, a radar chip may have dimensions of 8 mm by 6 mm by 2 mm or smaller and can include an antenna array that can be used to perform beam forming. By implementing such a small radar chip, radar capabilities can be incorporated into various electronic devices, such as smart-home devices, that can be strategically located in various environments throughout a home to monitor for a person falling. Such smart-home devices may be "semi-permanently" positioned within a home. By being semi-permanently positioned, the smart-home devices are not necessarily affixed to a surface, but are placed in a location where they can remain for significant stretches of time, such as several hours, days, weeks, or even years. Such semi-permanently positioned smart-home devices are in contrast to mobile devices, such as a smartphone or tablet computer, which tend to picked up, interacted with, and moved by a user frequently.

When a person has been detected within an environment monitored by a smart-home device having integrated fall detection, a radar chip of the smart-home device can be activated. The radar chip can emit electromagnetic radiation (also referred to as "radio waves") into the environment of the smart-home device. Reflected radio waves may be received by multiple antennas of the radar chip. Received raw waveform data may be output by the radar chip for processing by the smart-home device.

The smart-home device may perform processing locally or may transmit data to a cloud-based server for processing. The processing can include performing a clutter removal process to isolate raw waveform data corresponding to moving objects. Beam forming can be performed using the separate sets of raw waveform data obtained from each antenna of the antenna array. A moving object may be identified and tracked during a rolling window of time. The moving object may be reduced to a point and have its center-of-mass tracked. The movement of the center-of-mass of the object may be analyzed using a pre-trained machine learning model. The machine learning model may be trained to analyze some number of features of the center-of-mass, such as three, four, five, ten, or sixteen features. Characteristics of each of these features may be attributed to different weights by the trained model and can be used to determine whether the person has fallen.

If a fall has been detected, the smart-home device may attempt to ascertain whether one or more emergency contacts need to be alerted. The smart-home device may output audio in the form of speech via a speaker asking something similar to: "I have detected a fall. Do you need help?" The person who fell can then respond via speech. Since the home automation device is already active, no passphrase may be needed to activate listening capabilities of the home automation device. If the person responds that she is "OK", no further action may be taken by the home automation device. Alternatively, if the person responds that help is needed or a predefined amount of time expires without a response being received, the smart-home device may transmit an alert to an emergency contact. For instance, a push notification can be sent to a mobile device user that has been added as the emergency contact. Additionally or alternatively, an emergency service, such as 911, can be alerted that a fall has been detected, which may trigger the emergency service to perform a wellness check at the household.

Further detail regarding these and other embodiments is provided in relation to the figures. FIG. 1 illustrates an embodiment of an environment in which a person can be monitored for falls. In environment 100, elderly person 101 may live alone. Therefore, if a person is detected moving within the environment, it may be assumed to be elderly person 101 even though no identity determination is performed (e.g., no facial or voice recognition). In some embodiments, smart-home device 110 may have a display screen (e.g., touchscreen), a radar integrated circuit, but no optical camera. As such, smart-home device 110 can be placed in a location where a user would have privacy concerns if an optical camera was present. In other embodiments, smart-home device 110 may have an optical camera for other purposes (e.g., video chat).

Smart-home device 110 may be positioned such that a radar chip of smart-home device 110 has a field-of-view 120 of as much of environment 100 as possible. Smart-home device 110 may be placed on a shelf or some other semi-permanent location from where smart-home device 110 does not need to be frequently moved. For example, the smart-home device 110 may be affixed to a wall or ceiling. Such an arrangement can allow smart-home device 110 to monitor environment 100 as long as smart-home device 110 has power and is not moved. Therefore, monitoring for falls may be performed continuously in the room where smart-home device 110 is located. Smart home device 110 may be incorporated with another device that makes sense to have in the same location. For instance, smart home device 110 may be incorporated as part of a smart smoke and/or carbon monoxide detector and attached with the ceiling or smart home device 110 may be incorporated as part of wall clock 130 and attached with the wall.

In addition to monitoring for falls, smart-home device 110 may be able to monitor the pace of the monitored person's walking. As the monitored person's walking pace decreases, a determination can be made that she is becoming more feeble and more likely to fall. Over a significant amount of time, such as weeks, months, or even years, a trend in the monitored person's walking pace can be determined and output, such as to an emergency contact.

In some embodiments, monitoring of a person may be restricted to situations where only one person is detected as present. If multiple people are present and one person falls, the other person who has not fallen can likely provide significantly more help than smart-home device 110. Therefore, if multiple people are detected as present, fall detection and monitoring features of smart-home device 110 may be disabled until only one person is detected as either home (based on the entirety of a smart home ecosystem) or within the environment of smart-home device 110.

Figure 2:
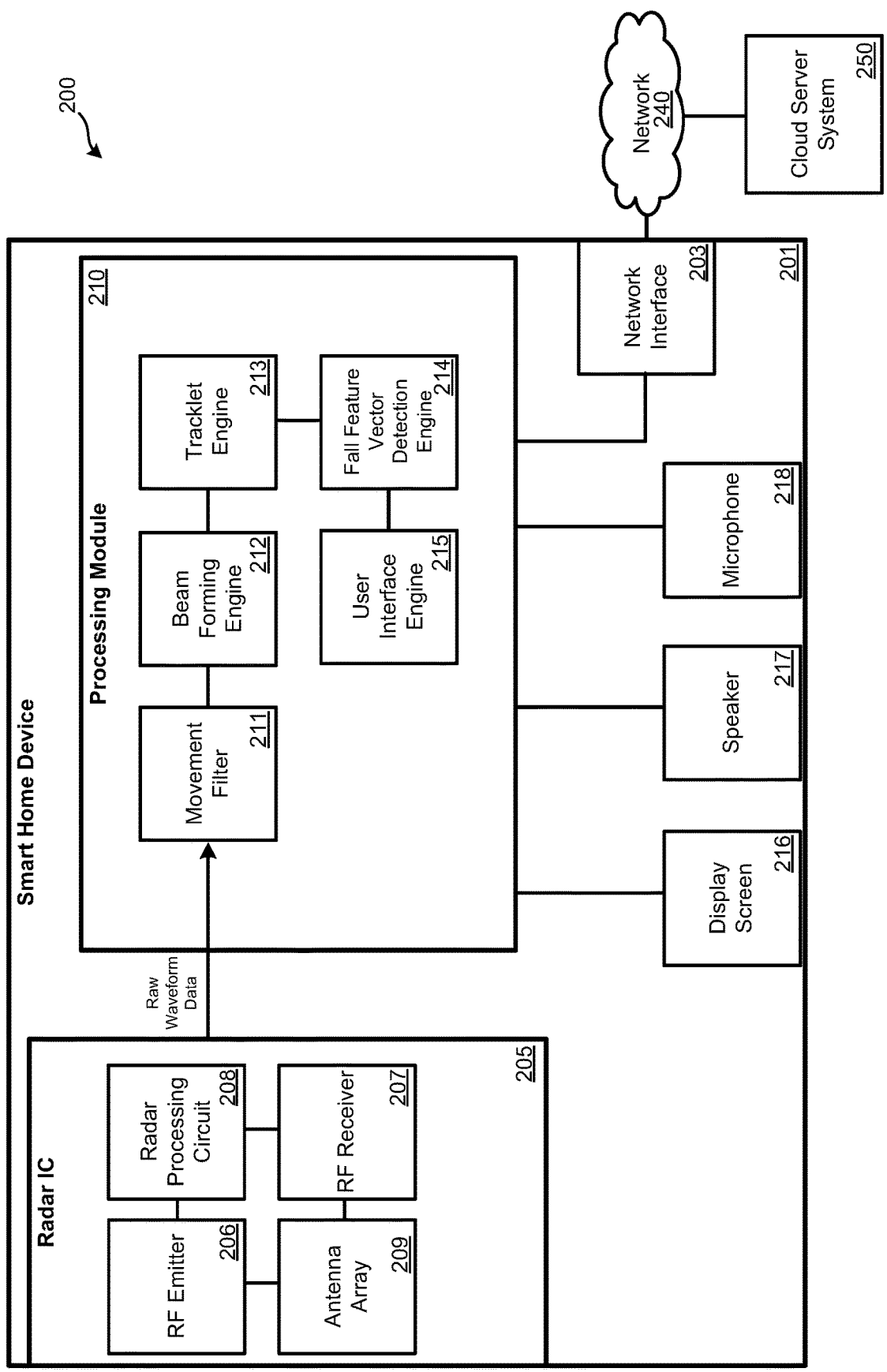
FIG. 2 illustrates a block diagram of an embodiment of a radar-based fall detection system.

FIG. 2 illustrates a block diagram of an embodiment of a radar-based fall detection system 200. Radar-based fall detection system 200 ("system 200") can include: smart-home device 201; network 240; and cloud server system 250.

Smart-home device 201 may be various types of smart-home devices, such as a smart home assistant device that can respond to spoken queries from persons nearby. A smart home assistant device may continuously listen for a spoken passphrase, which triggers the smart home assistant device to capture and analyze a spoken query. Various forms of smart-home devices which can function as smart-home device 201 are detailed in relation to FIG. 3. In other embodiments, fall detection processing and radar integrated circuit (IC) 205 may be incorporated into an electronic device other than a smart-home device.

Smart-home device 201 can include: network interface 203; radar IC 205; processing module 210; display screen 216; speaker 217; and microphone 218. Radar IC 205 can represent a monolithic integrated circuit. Therefore, all components of radar IC 205 are implemented within a single package that can be affixed to a printed circuit board of smart-home device 201. As an example of radar IC 205, Infineon® BGT60TR13C may be used. Radar IC 205 can include: RF emitter 206; RF receiver 207; radar processing circuit 208; and antenna array 209. Antenna array 209 may be incorporated as part of radar integrated circuit 205. Antenna array 209 can include multiple antennas. For example, in some embodiments, two, three, four, or more antennas are included as part of antenna array 209.

RF emitter 206 may generate radio waves or, more generally, electromagnetic radiation, into the ambient environment, the radio waves emitted may be frequency modulated continuous wave (FMCW) radar. For instance, the generated radio waves may be generated at or around 60 GHz. In other embodiments, the generated electromagnetic radiation may be at a frequency between 40 GHz and 100 GHz or between 50 GHz and 120 GHz. The generated radio waves may be emitted via antenna array 209 or a separate antenna that is part of RF emitter 206. By using such radio frequencies, it may be possible for radar IC 205 to be housed in a small package. For example, radar IC 205 may be 8 mm by 6 mm by 2 mm or smaller. By radar IC 205 being so small, it may be possible to incorporate radar IC 205 into many types of smart-home devices that are relatively small without increasing or significantly increasing the physical size of such smart-home devices.

RF receiver 207 may receive separate signals via each antenna of antenna array 209. Radar processing circuit 208, in combination with RF receiver 207, may produce raw waveform data for each antenna of antenna array 209. The raw data produced by radar processing circuit 208 can be referred to as raw waterfall data. While it may be possible for radar IC 205 to perform some processing on the raw waterfall data locally using radar processing circuit 208, it may also be possible for radar IC 205 to output the raw waterfall data for each antenna of antenna array 209. In the illustrated embodiment of system 200, the raw waterfall data for each antenna of antenna array 209 is output to processing module 210. Processing module 210 can represent one or more separate integrated circuits from radar IC 205.

While the illustrated embodiment of system 200 includes a monolithic IC that performs all of the radar functions, it should be understood that in other embodiments, components of radar IC 205 may be split among multiple components. For example, antenna array 209 may be located separately from RF emitter 206 and/or RF receiver 207.

Smart-home device 201 can include network interface 203. Network interface 203 can allow smart-home device 201 to communicate via one or more wired and/or wireless networks. For instance, network interface 203 may allow smart-home device 201 to communicate via a wireless local area network, such as a wireless network that operates in accordance with an IEEE 802.11 standard. Network interface 203 may also communicate via one or more mesh networking protocols, such as Thread, Zigbee, or Z-Wave.

Network interface 203 may permit smart-home device 201 to communicate with network 240. Network 240 can include one or more private and/or public networks, such as the Internet. Network 240 may be used such that smart-home device 201 can communicate with the cloud server system 250. Cloud server system 250 may, in some embodiments, perform some of the processing functions performed by processing module 210. Additionally or alternatively, cloud server system 250 may be used to relay notifications and/or store data produced by smart-home device 201. For instance, in association with the user account, fall alerts created by smart-home device 201 may be logged by cloud server system 250.

Display screen 216, speaker 217, and microphone 218 may permit smart-home device 201 to interact with persons nearby. Display screen 216 may be a touchscreen display that presents information pertinent to other smart-home devices that have been linked with smart-home device 201 and results obtained in response to a query posed by user via microphone 218. In some embodiments, smart-home device 201 may not have display screen 216. For instance, some forms of smart home assistants, which respond to auditory queries, use speech as the primary input and output interfaces.

Microphone 218 can be used for a person to pose a spoken query to smart-home device 201. The spoken query may be analyzed locally or may be transmitted by smart-home device 201 to cloud server system 250 for analysis. A result of the spoken query may be transmitted back to smart-home device 201 by cloud server system 250 to be output via speaker 217 using recorded or synthesized speech. Speaker 217 and microphone 218 may further be used to interact with a person when a fall has been detected. Further detail regarding interactions that may be performed using speaker 217 and microphone 218 when a fall by a person has been detected are detailed in relation to state diagram 700.

Processing module 210 may include one or more special-purpose or general-purpose processors. Such special-purpose processors may include processors that are specifically designed to perform the functions detailed herein. Such special-purpose processors may be ASICs or FPGAs which are general-purpose components that are physically and electrically configured to perform the functions detailed herein. Such general-purpose processors may execute special-purpose software that is stored using one or more non-transitory processor-readable mediums, such as random access memory (RAM), flash memory, a hard disk drive (HDD), or a solid state drive (SSD). The components that are presented as part of processing module 210 can be implemented as individual hardware and/or software components or may be implemented together, such as in the form of software that is executed by one or more processors.

The raw waveform data received for each antenna received from radar IC 205 may first be processed using movement filter 211. Movement filter 211 may be used to separate static background radar reflections from moving objects. Since fall detection is inherently based on detecting an object that is moving, radar reflections due to static objects can be filtered out and discarded. Therefore, movement filter 211 may buffer raw waterfall data for each antenna individually for a rolling time window, such as between one and five seconds. Since static objects can be expected to produce the same radar reflections repeatedly, and adaptive background subtraction process may be performed for each set of raw waterfall data. The output from movement filter 211 may be foreground waterfall data for each antenna. Data included in the foreground waterfall data corresponds to only radar reflections from objects that have moved during the rolling time window.

Figure 4:
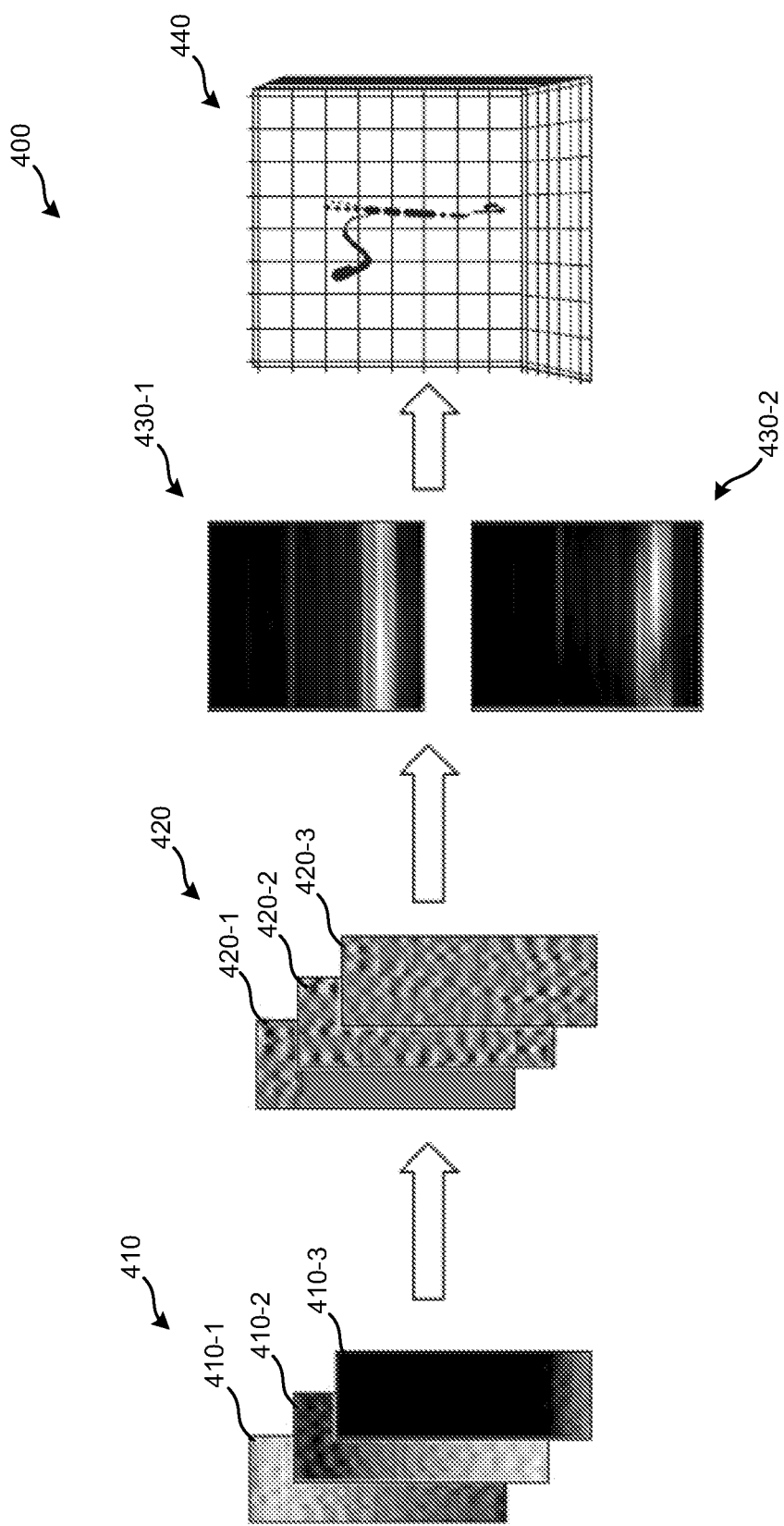
FIG. 4 illustrates an embodiment of raw received radar data being converted into a tracklet that can be used for fall detection.

The output foreground waterfall data for which a set of foreground waterfall data corresponds to each antenna of antenna array 209, may be passed to beam forming engine 212. Beam forming engine 212 may be used to determine the angle and distance to an object in motion that reflected radar. Beam forming may be performed by comparing differences in the time at which the radar reflections were received by each antenna. Multiple three-dimensional fast Fourier transforms (FFTs) may be performed to produce heat map projections, an example of which is illustrated in FIG. 4.

To perform the beam forming, waterfalls from two channels are stacked to create a three dimensional data block. Two combinations may be performed (e.g., a waterfall data from a first antenna and a second antenna, and waterfall data from a second antenna and a third antenna if there are three receivers or one waterfall from one set of linearly arranged antennas and another waterfall from another set of linearly arranged antennas where the two sets of antennas don't form parallel lines). Therefore, two three dimensional data blocks may now be present. A FFT may on each of the three dimensional data blocks. Zero padding may be used to improve output data quality. Data may be summed (or marginalized) over one of the dimensions to create two two-dimensional data sets. The result is intensity data as indicated in heat maps 430. In an alternate implementation, we can choose not to marginalize that dimension which could give us additional features for modeling, such as velocity features.

In an alternative embodiment of beam forming, rather than creating three dimensional data then marginalizing, two dimensional data may be created from the start. For such an embodiment, waterfall data may not be initially stacked, thus resulting in two dimensional data being directly obtained.

Each heat map may be indicative of: an amount of reflected radio waves; a range to the object that reflected the radio waves; and an angle from antenna array 209 to the object that reflected the radio waves. Therefore, for example a first heat map may be produced that indicates the range and the azimuthal angle to the object that reflected radio waves and a second heat map may be produced that indicates the range and elevational angle to the object that reflect radio waves.

The heat maps created by beam forming engine 212 may be output to tracklet engine 213. Tracklet engine 213 may combine information from the multiple heat maps produced by beam forming engine 212 to track a center-of-mass of an object. The center of mass can be extracted using an average location of the brightest intensity points in the image. In some embodiments, a process called non-maximum suppression (NMS) is used. If clustered high intensity points are smaller than a defined size threshold, the points may be discarded as being related to too small of an object to be a person. For instance, a moving object may be a clock pendulum or a breeze moving leaves of a plant. Since such movement is unrelated to a person, may be desirable to suppress or otherwise remove movement attributed to such nonperson objects.

Tracklet engine 213 may represent the identified moving object, which is expected to be a person, as a single center-of-mass as obtained from the averaging or NMS process. Therefore, a single point can be used to represent an entire person with the single point being located in space at or near the center-of-mass of the person. The center-of-mass tracking may be performed by tracklet engine 213 by applying non-maximum suppression (NMS) and, possibly, an unscented Kalman filter (UKF). It should be understood that in other embodiments, different forms of filtering may be performed by tracklet engine 213.

An example output of tracklet engine 213 is provided in FIG. 4 and FIG. 5. The output of tracklet engine 213 may be a three-dimensional map of the movement of a center-ofmass represented as a vector over a historic window of time, such as five or ten seconds. Use of a three-dimensional map may be particularly important sense a person may be moving towards or away from smart-home device 201 and/or may be moving laterally with respect to smart-home device 201. When the person falls, the person can be expected to fall generally downward.

The tracklet map of the movement of the center-of-mass over the historic time window may be output to fall feature vector detection engine 214. This tracklet map can be understood as a vector moving over the historic time window. Fall feature vector detection engine 214 may be a pre-trained machine learning model. The pre-trained machine learning model may perform event classification based on the historical map. The pre-trained machine learning model may be based on a random forest machine learning model. However, it should be understood that other forms of machine learning models are possible, such as a neural network based machine learning model.

Fall feature vector detection engine 214 may analyze some number of features of the movement of the center-of-mass over the historic window of time. For example, in some embodiments more than four features of the movement of the center-of-mass over the historic window of time may be analyzed according to a pre-defined weighting by the pre-trained machine learning model. In some embodiments, between three and twenty features, such as sixteen features, of the center-of-mass may be analyzed by the pre-trained machine learning model. For example, these features can include: initial azimuthal position; final azimuthal position; azimuthal position change; azimuthal slope; initial elevational position; final elevational position; elevational position change; elevational slope; initial range position; final range position; range position change; range slope; initial RCS (radar cross section) position; final RCS position; RCS position change; RCS slope; and velocity. An "initial" position refers to the position at the beginning of the historic time window, a "final" position refers to the position at the end of the historic time window, a "change" position refers to the amount of change that has occurred in position in the specified direction over the historic time window; and "slope" refers to the rate of change in position in the specified direction over the historic time window. "Range" refers to position relative to a distance from smart-home device 201.

For the above features, it may be possible that individual features are analyzed over varying time windows. For instance, RCS features may be analyzed over a longer time window than azimuthal features.

Each of these features may be assigned different weights as part of the pre-trained machine learning model based on the determined relative importance for correctly identifying a person falling. The weightings may be assigned based on a training process that was performed using a training set of data that included data indicative of a person falling and data of a person that did not fall. The training process may have involved creating a machine learning model that can classify as many falls and non-falls accurately as possible. For instance, a training set of data that includes a large amount of data having a known classification (i.e., fall-present, no fall present) may be fed to a machine learning engine. The machine learning engine may create a machine learning model that accurately classifies as many of the falls and non-falls as possible. The machine learning model may be trained prior to being installed on smart-home device 201 such that the pre-trained machine learning model can be used on a large number of smart-home devices being manufactured. Therefore, once installed on processing module 210, the machine learning model of fall feature vector detection engine 214 may be static.

Separate machine learning models may be used depending on the type of location where the smart home device is to be placed. For instance, different machine learning models, that are trained separately, use different weightings, and/or different types of machine learning (e.g., a neural network) may be used based on the type of installation location, such as a wall or ceiling.

In other embodiments, the machine learning model may be dynamic in that it can learn about situations that involved and fall and non-fall after being installed in the environment in which the smart home device will function. For instance, if the machine learning model classifies a fall with a low confidence, it may seek feedback on whether its identification of the fall was correct. Depending on the feedback, the machine learning model may be adjusted to be more accurate for future fall detections.

The pre-trained machine learning model may include several features that are more heavily weighted than other features. For example, for a machine learning model for a smart home device that is to be attached with a wall or placed on a shelf, the three most heavily weighted features may be: final elevation position; elevation position change; and elevation slope. In some embodiments, only these three features may have a weighting greater than 0.10. The single most heavily weighted feature may be elevation position change. The elevation position change feature may be weighted greater than 0.25 or greater than 0.30 in some pre-trained machine learning models that use a random forest structure for performing a classification. For a smart home device that is to be attached to a ceiling, before and after range values may be highly weighted features.

The output of fall feature vector detection engine 214 may be an indication of whether or not a fall has likely occurred. If no fall has been detected, fall detection monitoring may continue and no action may be taken by smart-home device 201. If a fall is detected, an indication of the fall may be passed to user interface engine 215. User interface engine 215 may attempt to interact with the person who is fallen and, based on a response or lack of response from the person, may or may not take additional actions. Further detail regarding the potential actions are detailed in relation to FIGS. 6 and 7.

Figure 3:
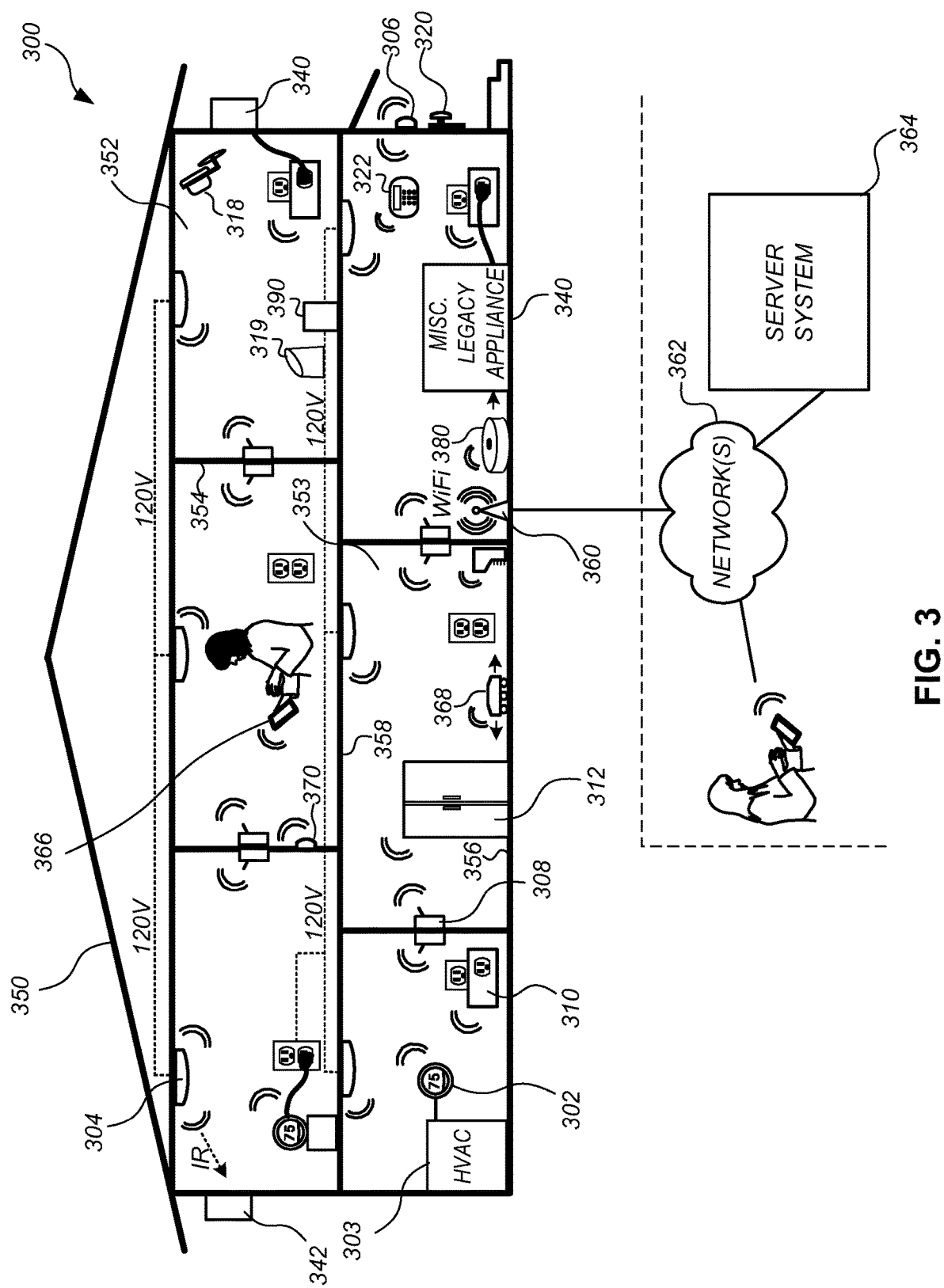
FIG. 3 illustrates a smart home environment that includes various smart-home devices in which radar-based fall monitoring can be integrated.

FIG. 3 illustrates an embodiment of a smart home environment 300 in which various smart-home devices may include the componentry of smart-home device 201 to perform fall detection. Various smart-home devices, including those located indoors or outdoors, may benefit from the ability to detect falls.

The smart home environment 300 includes a structure 350 (e.g., a house, daycare, office building, apartment, condominium, garage, or mobile home) with various integrated devices. It will be appreciated that devices may also be integrated into a smart home environment 300 that does not include an entire structure 350, such as an apartment or condominium. Further, the smart home environment 300 may control and/or be coupled to devices outside of the actual structure 350. Indeed, several devices in the smart home environment 300 need not be physically within the structure 350.

It is to be appreciated that "smart home environments" may refer to smart environments for homes such as a single-family house, but the scope of the present teachings is not so limited. The present teachings are also applicable, without limitation, to duplexes, townhomes, multi-unit apartment buildings, hotels, retail stores, office buildings, industrial buildings, and more generally any living space or work space.

It is also to be appreciated that while the terms user, customer, installer, homeowner, occupant, guest, tenant, landlord, repair person, and the like may be used to refer to the person or persons acting in the context of some particular situations described herein, these references do not limit the scope of the present teachings with respect to the person or persons who are performing such actions. Thus, for example, the terms user, customer, purchaser, installer, subscriber, and homeowner may often refer to the same person in the case of a single-family residential dwelling, because the head of the household is often the person who makes the purchasing decision, buys the unit, and installs and configures the unit, and is also one of the users of the unit. However, in other scenarios, such as a landlord-tenant environment, the customer may be the landlord with respect to purchasing the unit, the installer may be a local apartment supervisor, a first user may be the tenant, and a second user may again be the landlord with respect to remote control functionality. Importantly, while the identity of the person performing the action may be germane to a particular advantage provided by one or more of the implementations, such identity should not be construed in the descriptions that follow as necessarily limiting the scope of the present teachings to those particular individuals having those particular identities.

The depicted structure 350 includes a plurality of rooms 352, separated at least partly from each other via walls 354. The walls 354 may include interior walls or exterior walls. Each room may further include a floor 356 and a ceiling 358. Devices may be mounted on, integrated with and/or supported by a wall 354, floor 356 or ceiling 358.

In some implementations, the integrated devices of the smart home environment 300 include intelligent, multi-sensing, network-connected devices that integrate seamlessly with each other in a smart home network and/or with a central server or a cloud-computing system to provide a variety of useful smart home functions. The smart home environment 300 may include one or more intelligent, multi-sensing, network-connected thermostats 302 (hereinafter referred to as "smart thermostats 302"), one or more intelligent, network-connected, multi-sensing hazard detection units 304 (hereinafter referred to as "smart hazard detectors 304"), one or more intelligent, multi-sensing, network-connected entryway interface devices 306 and 320 and one or more intelligent, multi-sensing, network-connected alarm systems 322 (hereinafter referred to as "smart alarm systems 322"). Each of these devices may have the functionality of smart-home device 201 incorporated.

In some implementations, the one or more smart thermostats 302 detect ambient climate characteristics (e.g., temperature and/or humidity) and control an HVAC system 303 accordingly. For example, a respective smart thermostats 302 includes an ambient temperature sensor.

A smart hazard detector may detect smoke, carbon monoxide, and/or some other hazard present in the environment. The one or more smart hazard detectors 304 may include thermal radiation sensors directed at respective heat sources (e.g., a stove, oven, other appliances, a fireplace, etc.). For example, a smart hazard detector 304 in a kitchen 353 includes a thermal radiation sensor directed at a network-connected appliance 312. A thermal radiation sensor may determine the temperature of the respective heat source (or a portion thereof) at which it is directed and may provide corresponding black-body radiation data as output.

The smart doorbell 306 and/or the smart door lock 320 may detect a person's approach to or departure from a location (e.g., an outer door), control doorbell/door locking functionality (e.g., receive user inputs from a portable electronic device 366-1 to actuate the bolt of the smart door lock 320), announce a person's approach or departure via audio or visual means, and/or control settings on a security system (e.g., to activate or deactivate the security system when occupants go and come). In some implementations, the smart doorbell 306 includes some or all of the components and features of the camera 318-1. In some implementations, the smart doorbell 306 includes a camera 318-1, and, therefore, is also called "doorbell camera 306" in this document. Cameras 318-1 and/or 318-2 may function as a streaming video camera and the streaming audio device detailed in relation to various embodiments herein. Cameras 318 may be mounted in a location, such as indoors and to a wall or can be moveable and placed on a surface, such as illustrated with camera 318-2. Various embodiments of cameras 318 may be installed indoors or outdoors. Each of these types of devices may have the functionality of smart-home device 201 incorporated.

The smart alarm system 322 may detect the presence of an individual within close proximity (e.g., using built-in IR sensors), sound an alarm (e.g., through a built-in speaker, or by sending commands to one or more external speakers), and send notifications to entities or users within/outside of the smart home environment 300. In some implementations, the smart alarm system 322 also includes one or more input devices or sensors (e.g., keypad, biometric scanner, NFC transceiver, microphone) for verifying the identity of a user, and one or more output devices (e.g., display, speaker). In some implementations, the smart alarm system 322 may also be set to an armed mode, such that detection of a trigger condition or event causes the alarm to be sounded unless a disarming action is performed. Each of these devices may have the functionality of smart-home device 201 incorporated.

In some implementations, the smart home environment 300 includes one or more intelligent, multi-sensing, network-connected wall switches 308 (hereinafter referred to as "smart wall switches 308"), along with one or more intelligent, multi-sensing, network-connected wall plug interfaces 310 (hereinafter referred to as "smart wall plugs 310"). The smart wall switches 308 may detect ambient lighting conditions, detect room-occupancy states, and control a power and/or dim state of one or more lights. In some instances, smart wall switches 308 may also control a power state or speed of a fan, such as a ceiling fan. The smart wall plugs 310 may detect occupancy of a room or enclosure and control the supply of power to one or more wall plugs (e.g., such that power is not supplied to the plug if nobody is at home). Each of these types of devices may have the functionality of smart-home device 201 incorporated.

In some implementations, the smart home environment 300 of FIG. 3 includes a plurality of intelligent, multi-sensing, network-connected appliances 312 (hereinafter referred to as "smart appliances 312"), such as refrigerators, stoves, ovens, televisions, washers, dryers, lights, stereos, intercom systems, wall clock, garage-door openers, floor fans, ceiling fans, wall air conditioners, pool heaters, irrigation systems, security systems, space heaters, window AC units, motorized duct vents, and so forth. Each of these devices may have the functionality of smart-home device 201 incorporated. In some implementations, when plugged in, an appliance may announce itself to the smart home network, such as by indicating what type of appliance it is, and it may automatically integrate with the controls of the smart home. Such communication by the appliance to the smart home may be facilitated by either a wired or wireless communication protocol. The smart home may also include a variety of non-communicating legacy appliances 340, such as old conventional washer/dryers, refrigerators, and the like, which may be controlled by smart wall plugs 310. The smart home environment 300 may further include a variety of partially communicating legacy appliances 342, such as infrared ("IR") controlled wall air conditioners or other IR-controlled devices, which may be controlled by IR signals provided by the smart hazard detectors 304 or the smart wall switches 308.

In some implementations, the smart home environment 300 includes one or more network-connected cameras 318 that are configured to provide video monitoring and security in the smart home environment 300. The cameras 318 may be used to determine occupancy of the structure 350 and/or particular rooms 352 in the structure 350, and thus may act as occupancy sensors. For example, video captured by the cameras 318 may be processed to identify the presence of an occupant in the structure 350 (e.g., in a particular room 352). Specific individuals may be identified based, for example, on their appearance (e.g., height, face) and/or movement (e.g., their walk/gait). Cameras 318 may additionally include one or more sensors (e.g., IR sensors, motion detectors), input devices (e.g., microphone for capturing audio), and output devices (e.g., speaker for outputting audio). In some implementations, the cameras 318 are each configured to operate in a day mode and in a low-light mode (e.g., a night mode). In some implementations, the cameras 318 each include one or more IR illuminators for providing illumination while the camera is operating in the low-light mode. In some implementations, the cameras 318 include one or more outdoor cameras. In some implementations, the outdoor cameras include additional features and/or components such as weatherproofing and/or solar ray compensation. Such cameras may have the functionality of smart-home device 201 incorporated.

The smart home environment 300 may additionally or alternatively include one or more other occupancy sensors (e.g., the smart doorbell 306, smart door locks 320, touch screens, IR sensors, microphones, ambient light sensors, motion detectors, smart nightlights 370, etc.). In some implementations, the smart home environment 300 includes radio-frequency identification (RFID) readers (e.g., in each room 352 or a portion thereof) that determine occupancy based on RFID tags located on or embedded in occupants. For example, RFID readers may be integrated into the smart hazard detectors 304. Each of these devices may have the functionality of smart-home device 201 incorporated.

Smart home assistant 319 may have one or more microphones that continuously listen to an ambient environment. Smart home assistant 319 may be able to respond to verbal queries posed by a user, possibly preceded by a triggering phrase. Smart home assistant 319 may stream audio and, possibly, video if a camera is integrated as part of the device, to a cloud-based server system 364 (which represents an embodiment of cloud-based host system 200 of FIG. 2). Smart home assistant 319 may be a smart device through which non-auditory discomfort alerts may be output and/or an audio stream from the streaming video camera can be output. As previously noted, smart home assistant 319 may have the functionality of smart-home device 201 incorporated.

By virtue of network connectivity, one or more of the smart-home devices of FIG. 3 may further allow a user to interact with the device even if the user is not proximate to the device. For example, a user may communicate with a device using a computer (e.g., a desktop computer, laptop computer, or tablet) or other portable electronic device 366 (e.g., a mobile phone, such as a smart phone). A webpage or application may be configured to receive communications from the user and control the device based on the communications and/or to present information about the device's operation to the user. For example, the user may view a current set point temperature for a device (e.g., a stove) and adjust it using a computer. The user may be in the structure during this remote communication or outside the structure.

As discussed above, users may control smart devices in the smart home environment 300 using a network-connected computer or portable electronic device 366. In some examples, some or all of the occupants (e.g., individuals who live in the home) may register their portable electronic device 366 with the smart home environment 300. Such registration may be made at a central server to authenticate the occupant and/or the device as being associated with the home and to give permission to the occupant to use the device to control the smart devices in the home. An occupant may use their registered portable electronic device 366 to remotely control the smart devices of the home, such as when the occupant is at work or on vacation. The occupant may also use their registered device to control the smart devices when the occupant is actually located inside the home, such as when the occupant is sitting on a couch inside the home. It should be appreciated that instead of or in addition to registering portable electronic devices 366, the smart home environment 300 may make inferences about which individuals live in the home and are therefore occupants and which portable electronic devices 366 are associated with those individuals. As such, the smart home environment may "learn" who is an occupant and permit the portable electronic devices 366 associated with those individuals to control the smart devices of the home.

In some implementations, in addition to containing processing and sensing capabilities, smart thermostat 302, smart hazard detector 304, smart doorbell 306, smart wall switch 308, smart wall plug 310, network-connected appliances 312, camera 318, smart home assistant 319, smart door lock 320, and/or smart alarm system 322 (collectively referred to as "the smart-home devices") are capable of data communications and information sharing with other smart devices, a central server or cloud-computing system, and/or other devices that are network-connected. Data communications may be carried out using any of a variety of custom or standard wireless protocols (e.g., IEEE 802.15.4, Wi-Fi, ZigBee, 3LoWPAN, Thread, Z-Wave, Bluetooth Smart, ISA100.5A, WirelessHART, MiWi, etc.) and/or any of a variety of custom or standard wired protocols (e.g., Ethernet, HomePlug, etc.), or any other suitable communication protocol, including communication protocols not yet developed as of the filing date of this document.

In some implementations, the smart devices serve as wireless or wired repeaters. In some implementations, a first one of the smart devices communicates with a second one of the smart devices via a wireless router. The smart devices may further communicate with each other via a connection (e.g., network interface 360) to a network, such as the Internet. Through the Internet, the smart devices may communicate with a cloud-based server system 364 (also called a cloud-based server system, central server system, and/or a cloud-computing system herein). Cloud-based server system 364 may be associated with a manufacturer, support entity, or service provider associated with the smart device(s). In some implementations, a user is able to contact customer support using a smart device itself rather than needing to use other communication means, such as a telephone or Internet-connected computer. In some implementations, software updates are automatically sent from cloud-based server system 364 to smart devices (e.g., when available, when purchased, or at routine intervals).

In some implementations, the network interface 360 includes a conventional network device (e.g., a router), and the smart home environment 300 of FIG. 3 includes a hub device 380 that is communicatively coupled to the network(s) 362 directly or via the network interface 360. The hub device 380 is further communicatively coupled to one or more of the above intelligent, multi-sensing, network-connected devices (e.g., smart devices of the smart home environment 300). Each of these smart devices optionally communicates with the hub device 380 using one or more radio communication networks available at least in the smart home environment 300 (e.g., ZigBee, Z-Wave, Insteon, Bluetooth, Wi-Fi and other radio communication networks). In some implementations, the hub device 380 and devices coupled with/to the hub device can be controlled and/or interacted with via an application running on a smart phone, household controller, laptop, tablet computer, game console or similar electronic device. In some implementations, a user of such controller application can view the status of the hub device or coupled smart devices, configure the hub device to interoperate with smart devices newly introduced to the home network, commission new smart devices, and adjust or view settings of connected smart devices, etc. In some implementations the hub device extends capabilities of low capability smart devices to match capabilities of the highly capable smart devices of the same type, integrates functionality of multiple different device types—even across different communication protocols—and is configured to streamline adding of new devices and commissioning of the hub device. In some implementations, hub device 380 further includes a local storage device for storing data related to, or output by, smart devices of smart home environment 300. In some implementations, the data includes one or more of: video data output by a camera device, metadata output by a smart device, settings information for a smart device, usage logs for a smart device, and the like.

In some implementations, smart home environment 300 includes a local storage device 390 for storing data related to, or output by, smart devices of smart home environment 300. In some implementations, the data includes one or more of: video data output by a camera device (e.g., cameras 318 or smart doorbell 306), metadata output by a smart device, settings information for a smart device, usage logs for a smart device, and the like. In some implementations, local storage device 390 is communicatively coupled to one or more smart devices via a smart home network. In some implementations, local storage device 390 is selectively coupled to one or more smart devices via a wired and/or wireless communication network. In some implementations, local storage device 390 is used to store video data when external network conditions are poor. For example, local storage device 390 is used when an encoding bitrate of cameras 318 exceeds the available bandwidth of the external network (e.g., network(s) 362). In some implementations, local storage device 390 temporarily stores video data from one or more cameras (e.g., cameras 318) prior to transferring the video data to a server system (e.g., cloud-based server system 364).

Further included and illustrated in the exemplary smart home environment 300 of FIG. 3 are service robots 368, each configured to carry out, in an autonomous manner, any of a variety of household tasks. For some embodiments, the service robots 368 can be respectively configured to perform floor sweeping, floor washing, etc.

In some embodiments, a service robot may follow a person from room to room and position itself such that the person can be monitored while in the room. The service robot may stop in a location within the room where it will likely be out of the way, but still has a relatively clear field-of-view of the room. Service robots 368 may have the functionality of smart-home device 201 incorporated such that falls can be detected. Such an arrangement may have the advantage of allowing one service robot with the functionality of smart-home device 201 incorporated to monitor a person throughout multiple rooms or in a large space.

FIG. 4 illustrates an embodiment 400 of raw received radar data being processed into a tracklet that can be used for fall detection. The processing of embodiment 400 may be performed using system 200 of FIG. 2. Raw waterfall data 410 is indicative of the raw data output by the radar IC. Raw waterfall data 410-1 may be a set of data that corresponds to a first antenna; raw waterfall data 410-2 may be a set of data that corresponds to a second antenna; and raw waterfall data 410-3 may be a set of data that corresponds to a third antenna. If greater or fewer numbers of antennas are present as part of the radar IC's antenna array, there may be greater or fewer numbers of sets of raw waterfall data.

Foreground waterfall data 420 represents raw waterfall data 410 that has been filtered based on motion over a time period to remove radar reflections from static objects, such as by movement filter 211. Therefore, the radar reflections indicated in foreground waterfall data 420 is due to one or more objects that are in motion. As with raw waterfall data 410, each set of foreground waterfall data 420 can correspond to a different antenna of the radar IC's antenna array: Foreground waterfall data 420-1 may be a set of data that corresponds to a first antenna; foreground waterfall data 420-2 may be a set of data that corresponds to a second antenna; and foreground waterfall data 420-3 may be a set of data that corresponds to a third antenna.

Multiple heat maps that indicate the direction, range, velocity, and intensity of reflected radar of objects in motion may be created, such as by beam forming engine 212. The x-axis of each heat map may represent an angle from a reference direction of the radar IC's antenna device, the y-axis may represent range (distance) from the radar IC. Alternatively, the axes used for range and angle may be inverted. The intensity of the radar reflection received from the range and angle may be represented on the heat map based on the value at a particular coordinate within the map. In the illustrated example of embodiment 400, two heat maps 430 are produced: heat map 430-1, which can be based on the difference in time-of-arrival of reflected radar, between two or more antennas, can represent differences in radar reflections based on an azimuthal angle; and heat map 430-2, which can also be based on the difference in time-of-arrival of reflected radar, between two or more antennas, can represent differences in radar reflections based on an elevational angle. Such heat maps may require that the antenna array include at least three antennas to perform such time-of-flight measurements.

Data from heat maps 430 may be filtered such as to remove data corresponding to a moving object that is too large or too small to be a person. The remaining data present in heat maps 430 may be combined and buffered to create tracklet 440 that maps motion of a vector that represents a center-of-mass of the movement present in heat maps 430.

Such processing may be performed by a tracklet engine, such as tracklet engine 213 of FIG. 2. Tracklet 440 may represent a three-dimensional path which the center-of-mass has moved during a historic time window. For instance, tracklet 440 may represent movement of the center-of-mass over it time. Such as between two and fifteen seconds. In some embodiments, the historic time window is five seconds or 10 seconds.

FIG. 5 illustrates embodiments 500 of two tracklets. Tracklet 510 represents movement of a center-of-mass in three dimensions over time due to walking. Tracklet 520 represents movement of a center-of-mass in three dimensions over time due to the person falling. Therefore, when tracklet 520 is detected, one or more actions should be taken in response to detecting the fall. Points 501 and 503 represent the oldest center-of-mass locations presented and points 502 and 504 represent the most recent center-of-mass locations presented.

Tracklet 510, while no user-facing action may be taken in response to detecting that the person is walking, data may be obtained from tracklet 510. The local maximums and local minimums within tracklet 510 may be indicative of steps. That is, for each step, a local maximum and a local minimum may occur. The average number of steps that occur over the historic window of time may be tracked for a relatively period of time, such as several days, weeks, months, or even years. Long-term step averages may be calculated and compared to determine if the person's walking pace has changed over time. If the long-term step average decreases by more than a threshold amount, a notification may be output to the person, an administrator, or emergency contact that indicates that the person's ability to walk may be degrading. A slower walking pace may be indicative of frailty. Therefore, as the walking pace decreases, the person may be more at risk for falling.

Figure 6:
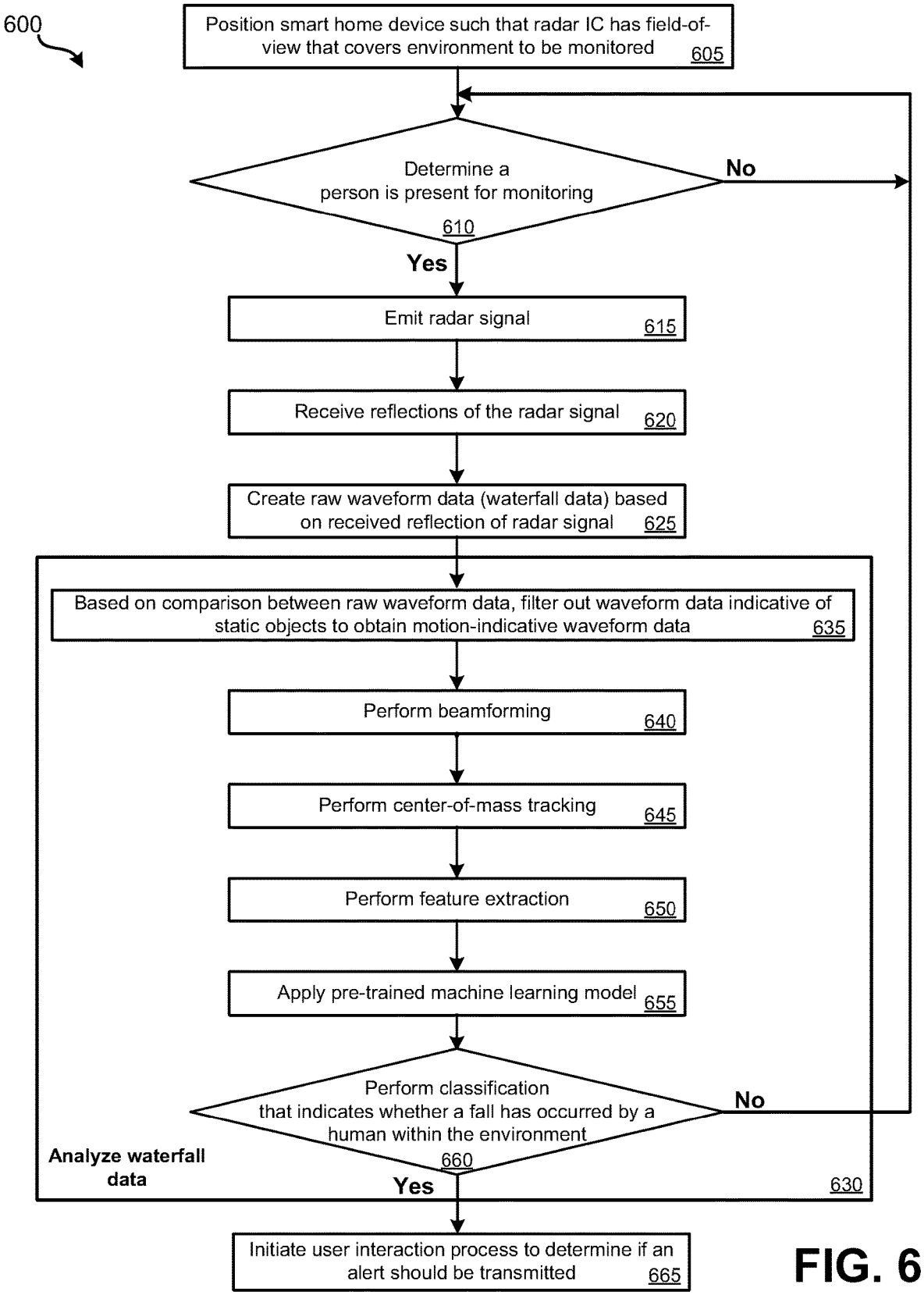
FIG. 6 illustrates a method for performing fall detection.

Various methods may be performed using the systems and embodiments of FIGS. 1-5. FIG. 6 illustrates a method 600 for performing fall detection. Blocks of method 600 may be performing using system 200. More specifically, blocks of method 600 may be performed using smart-home device 201 of FIG. 2.

At block 605, the smart-home device may be positioned such that the radar IC of the smart-home device has a field-of-view that includes the environment that is desired to be monitored. The smart-home device may be placed such that all or a significant portion of a room where a person can be expected to walk will be within the field-of-view of the radar IC of the smart-home device. Smart-home device may be placed semi-permanently, meaning that the smart-home device may remain in the location at which it was positioned for a significant period of time, such as at least several days. Such semi-permanent placement may be in contrast to a mobile device, such as a mobile phone or tablet computer that can be expected to be picked up, interacted with, and moved frequently.

At block 610, a determination may be made whether a person is present within the field-of-view of the radar IC. The determination of block 610 can be performed either using radar or some other presence detection technology, such as passive infrared presence detection. In some embodiments, one or more other smart-home devices may report whether the residence is likely occupied or not. A mobile device geofencing arrangement may also be used to determine if the person is present at the residence or is away. If the person is determined to not be present at block 610, the radar IC may be powered down or placed in a low-power mode that only periodically checks for movement. If the person is detected to be present, method 600 may proceed to block 615. A determination can also be made as to whether more than one person is present.

In some embodiments, at block 610, a determination may also be made if more than one person is present. If more than one person is determined to be present, fall monitoring may be disabled. In such a situation, monitoring may continue to occur to determine when only a single person is present. In some embodiments, fall detection may be enabled when only a single person has been determined to be present since if more than one person is present, help is already available if a person falls.

At block 615, radio waves, or more generally, electromagnetic radiation, may be emitted. Radio waves may be emitted at between 40 GHz and 80 GHz. In some embodiments, radio waves are emitted around 60 GHz. The emitted radio waves may be frequency modulated continuous wave radar. At block 620, reflections of the emitted radio waves may be received off of objects present within the field-of-view of the radar IC. The reflections may be received via multiple antennas of the radar IC (or via antennas separate from the radar processing circuitry).

At block 625, raw waveform data, which can be referred to as raw waterfall data, may be created and output by the radar IC for each antenna. The raw waterfall data is based on the received reflections of the emitted radio waves. The raw waterfall data may be provided to a processing system that will analyze the raw waterfall data to monitor for and identify a fall by a person.

At block 627, the waterfall data may generally be processed to determine if a person has fallen. The processing may be performed locally using a processing system of the smart-home device or may be performed remotely in the cloud by a cloud-based server system. At block 635, the raw waveform data may be buffered for a period of time, such as between one and 10 seconds. The raw waveform data may have an adaptive background subtraction process applied. This background subtraction process may identify static portions of the raw waterfall data and remove such portions such that raw foreground waterfalls are created that correspond to movement within the field-of-view of the radar IC.

At block 640, beam forming may be performed using the raw foreground waterfalls. Multiple heat maps may be produced based on the beam forming that identify the range and angle to the moving object that reflected the radio waves. For example, a first heat map may be indicative of an azimuthal angle and a second he met may be indicative of an elevational angle.

At block 645, the multiple heat maps may be combined in order to determine a location of a center-of-mass of the moving object. A tracklet may be produced that includes a vector that represents movement of the center-of-mass over a historic time window. For instance the tracklet may represent movement of the center-of-mass over a historic window of between one and fifteen seconds, such as five or ten seconds.

At block 650, a feature extraction process may be performed. The feature extraction process may identify some number of features of the tracklet determined at block 645. For instance, as previously detailed 10 or more features may be determined at block 650. In some embodiments, 16 features are determined. At block 655, a pre-trained machine learning model may receive the features identified at block 650. The pre-trained machine learning model may be a random forest machine learning model or some other form of machine learning model, such as a neural network. Based on the features provided to the pre-trained machine learning model, a classification may be performed that indicates whether the features represent a fall or not.

If at block 660 it is determined that no fall occurred at block 660, method 600 may return to block 610. Method 600 may continue to repeat and monitor any person present for a fall. If at block 660 it is determined that a fall did occur at block 660, method 600 may proceed to block 665. At block 665, a user interaction process may be initiated that determines what, if any, actions should be taken by the smart-home device in response to the fall being detected. Further detail regarding the user interaction process of block 665 is provided in relation to FIG. 7.

Figure 7:
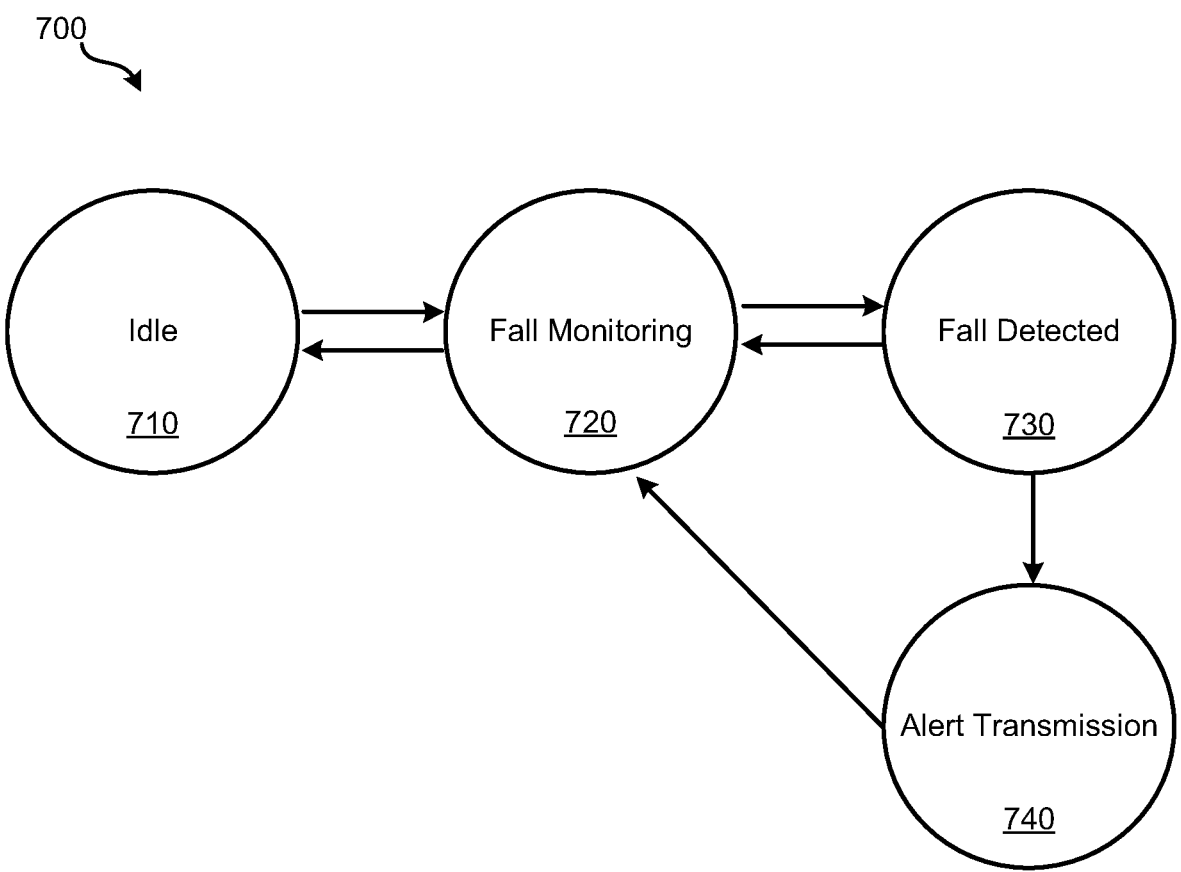
FIG. 7 illustrates an embodiment of various states in which a radar-based fall detection system may function.

FIG. 7 illustrates a diagram 700 of various states in which a radar-based fall detection system may function. State 710 represents that fall monitoring of the smart-home device is not being performed. State 710 may represent the current state of the smart-home device when either no person has been detected as present or multiple persons are present. The number of persons may be detected on a household level or within the field-of-view of the smart-home device. If a person is present and, in some embodiments, if exactly one person is present, state 720 may be the current state of the smart-home device, which indicates that fall monitoring and detection is active. Method 600 may be performed repeatedly while fall monitoring is active at state 720. If a fall is detected, state 730 may be entered. When state 730 is entered, a user interaction process may begin.

In some embodiments, the smart-home device uses auditory communication to communicate with the person who is fallen. Auditory communication may be preferable because if the person is fallen, they may be unable to reach or otherwise interact with the smart-home device. In initial auditory communication by the smart-home device may be output in the form of synthesized or recorded speech. Smart-home device may output something to the effect of: "A fall has been detected. Do you need any help?" Therefore, the smart-home device may explicitly request that a response be provided, such as by the person who has fallen by speaking a response.

The smart-home device may then wait up to a predefined amount of time for a response. Using a microphone of the smart-home device, the smart-home device may listen for a response. A spoken response received by the smart-home device may be analyzed locally or transmitted to a cloud-based server for analysis. If the spoken response indicates that no help is needed, the smart-home device may return to state 720. In some embodiments, the smart-home device may output and auditory response confirming that the smart-home device will take no further actions. For example, the smart-home device may respond: "OK. I won't contact anyone. I hope you are OK."

If the spoken response indicates that help is needed or no response is received within the predefined amount of time, the smart-home device may enter state 740. At state 740, one or more alerts may be transmitted. In some embodiments, a text message or push alert is sent to an emergency contact that is been previously linked with the fall detection feature of the smart-home device. For instance, a user account linked to the smart-home device stored by the cloud based server may indicate the emergency contact that should receive one or more alerts about the fall. For example, the alert sent may indicate: "A fall was detected at Margret's home and she indicated that she needs help." In some embodiments, the recipient of the alert may be required to acknowledge that the alert has been received. Additionally or alternatively, the alert may be sent to one or more additional emergency contacts or may only be sent if the primary emergency contact fails to acknowledge receipt of the alert. The smart-home device may be able to open a two-way communication link (e.g., a telephone call) via the person who has fallen and one or more of the emergency contacts. Such an arrangement may allow the person who is fallen to speak with his or her emergency contact via the speaker and microphone of the smart-home device.

In some embodiments, an alert may be sent to an emergency service provider, such as the local fire department. The smart-home device may be able to contact and open a two way call between the person who has fallen and the emergency service provider. In some embodiments, the smart-home device may first request authorization to call the emergency service provider from the person who is fallen. For instance, the smart-home device may output speech such as: "OK, you need help. Should I call an ambulance?" The action taken by the smart-home device may be based on the response of the person who has fallen. In some embodiments, as part of state 740, the smart-home device may cause other smart-home devices within the residence to output, such as synthesized or recorded speech, indicating that a person has fallen in a particular room. For instance, the speech may be: "A fall has been detected in the living room." Therefore, if someone else is at the residence, that person may be able to assist the person who has fallen. After state 740 has been completed, the smart-home device may return to being in state 720. When no person or more than one person is detected in the presence of the smart-home device, the state of the smart-home device may be set to state 710.

The methods, systems, and devices discussed above are examples. Various configurations may omit, substitute, or add various procedures or components as appropriate. For instance, in alternative configurations, the methods may be performed in an order different from that described, and/or various stages may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Having described several example configurations, various modifications, alternative constructions, and equivalents may be used without departing from the spirit of the disclosure. For example, the above elements may be components of a larger system, wherein other rules may take precedence over or otherwise modify the application of the invention. Also, a number of steps may be undertaken before, during, or after the above elements are considered.

What is claimed is:

1. A smart-home device with integrated fall detection, the smart-home device comprising:
a housing;
a speaker within the housing;
a microphone within the housing;
a monolithic radar integrated circuit that comprises an antenna array for receiving reflected radar, wherein:
the monolithic radar integrated circuit is housed by the housing; and
a processing system, comprising one or more processors, that is in communication with the monolithic radar integrated circuit, the processing system being configured to:
receive raw waveform data from the radar integrated circuit;
filter, from the raw waveform data, waveform data indicative of static objects to obtain motion-indicative waveform data;
perform center-of-mass tracking on a moving object present within the motion-indicative waveform data;
classify the moving object based on the center-of-mass tracking using a pre-trained machine learning model;
determine that a fall by a person has occurred; and
output an indication that the fall has been detected.

2. The smart-home device with integrated fall detection of claim 1, wherein the monolithic radar integrated circuit has dimensions of less than 8 mm by 6 mm by 2 mm.

3. The smart-home device with integrated fall detection of claim 2, wherein the processing system being configured to output the indication comprises the processing system being configured to cause the speaker of the smart-home device to output speech announcing that the fall has been detected and request that an auditory response be provided.

4. The smart-home device with integrated fall detection of claim 3, wherein the processing system is further configured to receive an auditory response via the microphone and process the auditory response.

5. The smart-home device with integrated fall detection of claim 4, wherein the processing system is further configured to perform an action in response to the auditory response, wherein the action is selected from the group consisting of:
transmit a communication via a wireless network to an emergency contact; and
output a spoken message indicating that no further action is to be taken.

6. The smart-home device with integrated fall detection of claim 5, wherein the monolithic radar integrated circuit emits frequency-modulated continuation wave (FMCW) radio waves.

7. The smart-home device with integrated fall detection of claim 1, wherein the smart-home device is a home assistant device.

8. The smart-home device with integrated fall detection of claim 1, wherein the processing system being configured to output an indication that the fall has been detected is based on the processing system classifying the moving object based on the center-of-mass tracking using the pre-trained machine learning model.

9. The smart-home device with integrated fall detection of claim 8, wherein the processing system being configured to classify the moving object based on the center-of-mass tracking using the pre-trained machine learning model comprises applying a random forest pre-trained machine learning model.

10. The smart-home device with integrated fall detection of claim 9, wherein the pre-trained machine learning model as installed on the smart-home device is static and was created based on a training set of data indicative of situations in which a person has fallen and in which a person has not fallen.

11. The smart-home device with integrated fall detection of claim 8, wherein the processing system being configured to perform center-of-mass tracking comprises the processing system being configured to perform center-of-mass tracking over a rolling historic time period window.

12. The smart-home device with integrated fall detection of claim 11, wherein the rolling historic time period window is between one and fifteen seconds.

13. The smart-home device with integrated fall detection of claim 8, wherein the processing system is further configured to create a plurality of heat maps based on the motion-indicative waveform data, wherein each heat map of the plurality of heat maps is indicative of detected motion at a plurality of distances in a plurality of directions along a particular axis.

14. The smart-home device with integrated fall detection of claim 8, wherein the processing system being configured to receive the raw waveform data comprises the processing system being configured to receive a plurality of individual sets of raw waveform data from a plurality of antennas of the antenna array of the monolithic radar integrated circuit.

15. The smart-home device with integrated fall detection of claim 8, wherein the processing system being configured to classify the moving object is performed by the processing system based on at least four physical features of the center-of-mass tracking.

16. The smart-home device with integrated fall detection of claim 1, wherein the monolithic radar integrated circuit emits radar at greater than 40 GHz.

17. A method for performing fall detection, the method comprising:
positioning a home assistant device with a room such that the home assistant device is intended to remain stationary, wherein the home assistant device comprises:
a speaker;
a microphone; and
a monolithic radar integrated circuit that comprises an antenna array for receiving reflected radar;
transmitting, by the home assistant device, radar waves within the room;
based on reflected radar waves within the room, creating raw waveform data;
filtering, from the raw waveform data, waveform data indicative of static objects to obtain motion-indicative waveform data;
performing center-of-mass tracking on a moving object present within the motion-indicative waveform data;
classifying the moving object based on the center-of-mass tracking using a pre-trained machine learning model;
determining that a fall by a person has occurred based on classifying the moving object; and outputting, by the home assistant device, speech announcing that the fall has been detected via the speaker of the home assistant device.

18. The method for performing fall detection of claim 17, the method further comprising:

receiving an auditory response via the microphone of the home assistant device;

performing an action in response to the auditory response, wherein the action is selected from the group consisting of:

transmitting a communication via a wireless network to an emergency contact; and outputting a spoken message indicating that no further action is to be taken.

19. The method for performing fall detection of claim 17, wherein classifying the moving object based on the center-of-mass tracking using the pre-trained machine learning model comprises applying a random forest pre-trained machine learning model.

* * * * *